United States Patent
Hunter et al.

(12) 
(10) Patent No.: US 10,483,001 B2
(45) Date of Patent: Nov. 19, 2019

(54) INTERACTIVE DISPLAY FOR USE IN OPERATING ROOMS

(71) Applicant: CV Medical, Beaverton, OR (US)

(72) Inventors: John Hunter, Portland, OR (US); Paul White, Beaverton, OR (US)

(73) Assignee: Compview Medical, Beaverton, OR (US)

( * ) Notice: Subject to any disclaimer, the term of this patent is extended or adjusted under 35 U.S.C. 154(b) by 285 days.

(21) Appl. No.: 15/419,935

(22) Filed: Jan. 30, 2017

(65) Prior Publication Data

US 2017/0140113 A1  May 18, 2017

Related U.S. Application Data

(63) Continuation of application No. 13/830,757, filed on Mar. 14, 2013, now abandoned.

(Continued)

(51) Int. Cl.
| | |
|---|---|
| *G16H 40/20* | (2018.01) |
| *G09G 5/00* | (2006.01) |
| *G06F 3/147* | (2006.01) |
| *G06F 19/00* | (2018.01) |
| *G06Q 10/06* | (2012.01) |
| *G06Q 10/08* | (2012.01) |
| *G06Q 10/10* | (2012.01) |
| *G06Q 50/22* | (2018.01) |
| *A61B 34/00* | (2016.01) |

(Continued)

(52) U.S. Cl.
CPC ............ *G16H 40/20* (2018.01); *A61B 34/25* (2016.02); *G06F 3/0482* (2013.01); *G06F 3/0488* (2013.01); *G06F 3/147* (2013.01); *G06F 19/3481* (2013.01); *G06Q 10/0631* (2013.01); *G06Q 10/0833* (2013.01); *G06Q 10/1091* (2013.01); *G06Q 50/22* (2013.01); *G09G 5/003* (2013.01); *G16H 10/20* (2018.01); *G16H 10/60* (2018.01); *G16H 40/63* (2018.01); *G09G 2354/00* (2013.01); *G09G 2380/08* (2013.01)

(58) Field of Classification Search
CPC ............................. G16H 40/20; G06F 3/0488
USPC ....................................................... 340/10.6
See application file for complete search history.

(56) References Cited

U.S. PATENT DOCUMENTS

| | | | |
|---|---|---|---|
| 7,962,544 B2 | 6/2011 | Torok et al. | |
| 2005/0149358 A1* | 7/2005 | Sacco | G06F 19/328 |
| | | | 705/2 |

(Continued)

OTHER PUBLICATIONS

Brintzenhoff, et al., "Optimizing Operating Room Time Efficiency—Additional Obstacles to Efficient Case Flow," *Journal of Surgical Research*, 158(2), Feb. 2010, p. 369.

(Continued)

*Primary Examiner* — Vernal U Brown
(74) *Attorney, Agent, or Firm* — Klarquist Sparkman, LLP

(57) ABSTRACT

An interactive method of displaying information in an operating room can include receiving data via a reader from badges associated with persons to establish the presence of persons in the operating room or the like. The data can be processed and the identifying information can be displayed on a display device that is visually accessible within the operating room. The display device can also display other relevant information, including surgical pause checklists, retained object counts, and relevant medical data.

15 Claims, 6 Drawing Sheets

Related U.S. Application Data

(60) Provisional application No. 61/638,996, filed on Apr. 26, 2012.

(51) Int. Cl.
    *G16H 10/60*      (2018.01)
    *G16H 40/63*      (2018.01)
    *G16H 10/20*      (2018.01)
    *G06F 3/0482*     (2013.01)
    *G06F 3/0488*     (2013.01)

(56) References Cited

U.S. PATENT DOCUMENTS

| | | |
|---|---|---|
| 2005/0261942 A1 | 11/2005 | Wheeler |
| 2006/0119481 A1 | 6/2006 | Tethrake et al. |
| 2007/0129983 A1 | 6/2007 | Scherpbier et al. |
| 2007/0216526 A1 | 9/2007 | Volpi |
| 2008/0058612 A1* | 3/2008 | Ohyu .................. G16H 50/50 600/300 |
| 2008/0164998 A1 | 7/2008 | Scherpbier et al. |
| 2009/0144143 A1 | 6/2009 | Iyer |
| 2009/0178685 A1* | 7/2009 | Haines ................ A61B 5/411 128/852 |
| 2010/0332255 A1* | 12/2010 | Rotunda ............... G06Q 10/10 705/3 |
| 2011/0094521 A1 | 4/2011 | Haines et al. |
| 2012/0140068 A1 | 6/2012 | Monroe et al. |
| 2013/0073363 A1 | 3/2013 | Boal |
| 2015/0324681 A1 | 11/2015 | Mats |

OTHER PUBLICATIONS van Klei, et al., "Effects of the Introduction of the WHO "Surgical Safety Checklist" on In-Hospital Mortality," *Annals of Surgery*, 255(1), Jan. 2012, pp. 44-49.

Zalud, Bill, "Intelligent Reception," *Security*, 41(6), Jun. 2004, pp. 14-16.

\* cited by examiner

FIG. 2

WHO'S IN THE ROOM

ATTENDING ANESTHESIOLOGIST:
Ed K.      Time in: 10:33AM

ANESTHESIA RESIDENT/CRNA:

ATTENDING SURGEON:
John Hunter      Time in: 10:41AM

SURGERY RESIDENT:
Erin G.      Time in: 10:30AM
Tom M.      Time in: 10:35AM

CIRCULATOR RN:
Will G.      Time in: 10:33AM

SCRUB TECH/RN:
Darryl L.      Time in: 10:33AM

STUDENT/OTHERS:
Carson B.

| | |
|---|---|
| ATTENDING ANESTHESIOLOGIST | Ed K. |
| ANESTHESIA RESIDENT/CRNA | Darryl L. |
| ATTENDING SURGEON | Enter Name |
| SURGERY RESIDENT | Enter Name |
| CIRCULATOR RN | |
| SCRUB TECH/RN | |
| STUDENT/OTHERS | |

Keyboard
Brown, Jeff
Diehl, Chris
Jones, Edward
Neumann, AJ
Smith, Paul
Vincent, Peter
Williams, Carl Print   Save   Clear all

Surgical Pause Verification Summary

| | | |
|---|---|---|
| 1 | *Circulator: Attention everyone!*<br>*MD:* This is (Patient name).<br>*Circulator:* I confirmed this patient by name and date of birth on the ID band. | ✓ 10:44 |
| 2 | *MD:* We are doing (Procedure/Side/Site as stated on the consent). The estimated time to complete this case is (hours/minutes). The critical steps during which personnel should not be changed are (mentioned). | ✓ 10:44 |
| 3 | *Circulator:* Is the site marking visible? *(Must have concurrence from ALL present.)* | ✓ 10:46 |
| 4 | *MD:* We agree that the patient is in the correct position. *(Must have concurrence from ALL present.)* | ✓ 10:47 |
| 5 | *MD:* Are X-rays and other studies properly labeled and displayed? *(Must have concurrence from ALL present.)* | NA 10:48 |
| 6 | *Circulator:* Does this patient have any history, condition or medication use that is relevant to this procedure. (i.e., allergies, cardiac history possible requiring application of defib paddles, etc.) *(Must have concurrence from ALL present.)* | ✓ 10:48 |
| 7 | *MD:* What pre-op antibiotics have been given? *(Response from Anesthesia provider.)* | ✓ 10:50 |
| 8 | *Circulator:* Are fluids needed for irrigation? *(Response from Surgeon.)* | ✓ 10:51 |
| 9 | *MD:* Have all baseline counts been completed? *Response from Scrub: YES, NO, N/A* | ✓ 10:51 |
| 10 | *MD:* Does anyone have any additional questions or concerns? *(Must have concurrence from ALL present.)* | ✓ 10:53 |
| 11 | Repeat these steps with each Surgical Attending change. | ✓ 10:54 |

*PLEASE INFORM THE SURGEON/TEAM OF ANY PERSONNEL CHANGES AND TRANSFER OF CARE (e.g., CRNA ⇒ ANESTHESIOLOGIST, SURGEON ⇒ SURGEON, CIRCULATOR ⇒ CIRCULATOR, SCRUB ⇒ SCRUB, etc.)*

FIG. 4

Surgical Pause Verification Summary

| | |
|---|---|
| 1 | *Circulator:* Attention everyone!<br>*MD:* This is (Patient name).<br>*Circulator:* I confirmed this patient by name and date of birth on the ID band. |
| 2 | *MD:* We are doing (Procedure/Side/Site as stated on the consent). The estimated time to complete this case is (hours/minutes). The critical steps during which personnel should not be changed are (mentioned). |

— 12

PHYSICIAN'S SURGERY & PROCEDURE CONSENT FORM

FIG. 5

| Object Name | Open Packages Current Count |
|---|---|
| Lap Sponges | 5 |
| Ray-Tec Sponges | 10 |
| Knife Blades | 2 |
| Bovie Tip | 1 |
| Suction Tip | 1 |
| Hypo Needle | 1 |

| Object Name | In Patient Current Count |
|---|---|
| Bovie Tip | 1 |
| Ray-Tec Sponges | 0 |
| Knife Blades | 1 |
| Bovie Tip | 1 |
| Lap Sponges | 2 |

*Goal: The patient is free from unintended Retained Surgical Instruments*

FIG. 7

INTERACTIVE DISPLAY FOR USE IN OPERATING ROOMS

CROSS REFERENCE TO RELATED APPLICATION

This application is a continuation of U.S. application Ser. No. 13/830,757, filed on Mar. 14, 2013, which claims the benefit of U.S. Provisional Application No. 61/638,996, filed Apr. 26, 2012, which is hereby incorporated by reference in its entirety.

FIELD

The present disclosure is directed to methods and systems for displaying information relating to medical interventions, such as surgical procedures.

BACKGROUND

Most operating rooms have one or more permanent "whiteboards" where patient information and details relating to the surgical procedure are handwritten by hospital staff. Such information can include, for example, the name of the patient, the type of surgery that is being performed and the names of the medical personnel in the room. However, since the information on such whiteboards must be handwritten onto the whiteboard by operating room staff, errors can be introduced on the whiteboard during the transcription process. Moreover, anytime a change occurs relating to information that is currently presented on the whiteboard (e.g., the arrival or departure of medical personnel), the whiteboard must be manually updated by hospital staff in order to remain accurate.

SUMMARY

The various systems and methods disclosed herein relate to interactive systems for displaying information in, for example, operating rooms and other similar environments.

In one embodiment, an interactive method of displaying information in an operating room in connection with a surgical procedure is provided. The method includes receiving data via a reader from one or more badges associated with one or more respective persons to establish the presence of the one or more persons in the operating room, with the data containing identifying information relating to the one or more persons. The data is processed and the identifying information is displayed on a display device that is visually accessible within the operating room. The identifying information can include at least a name of the one or more persons and a role assigned to the one or more persons for the surgical procedure.

In some embodiments, the method includes logging a time associated with the receipt of data by the reader from the one or more badges and displaying the logged time along with the respective name and role of the one or more persons displayed on the display device. In other embodiments, the method includes entering information on a touchscreen device relating to one or more additional persons to establish the presence of the one or more additional persons in the room and displaying the name and the role of the one or more additional persons on the display device.

In other embodiments, the method can include retrieving one or more surgical pause checklists, selecting one of the one or more surgical pause checklists, and displaying the selected surgical pause checklist on the display device. The act of retrieving the one or more surgical pause checklists can include identifying surgical pause checklists associated with at least one of the one or more persons in the operating room and retrieving the identified surgical pause checklists. In some embodiments, the method includes displaying the surgical pause checklist on a touchscreen device, receiving inputs on the touchscreen device relating to a completion of one or more events on the surgical pause checklist, and altering the displayed surgical pause checklist displayed on the display screen to reflect the inputs received on the touchscreen device.

In some embodiments, foreign objects can be tracked using the system by displaying on the display device a first count of foreign objects that have been opened and are available for use during the surgical procedure. The display device can also display a second count of the foreign objects from the first count that have actually been used during the surgical procedure. Information about the foreign objects can be entered on a touchscreen device to determine the first and second counts displayed on the display device.

In some embodiments, patient data can be retrieved from a medical records system and at least a portion of the patient data can be selected using a touchscreen device. The selected portion of the patient data can be displayed on the display device. In some embodiments, the display screen can additionally display (simultaneously or separately) at least one of (1) a surgical pause checklist and (2) a foreign object count while displaying the identifying information on the display device.

In another embodiment, an interactive display system for use in an operating room in connection with a surgical procedure on a patient is provided. The system can include a reader configured to capture data contained on a badge carried by members of a medical team using one or more sensing parameters. The system can also include a processor configured to process the data read by the reader to determine respective identities of the members and respective roles of the members for a surgical procedure. A display device can be provided and configured to receive and display the identities and roles of the members.

In some embodiments, the system can further include a touchscreen device coupled to the processor and a storage device for storing additional information thereon. The touchscreen device can be configured to receive inputs from a user to select one or more of the additional information stored on the storage device for display on the display device. The additional information stored on the storage device can include a plurality of surgical pause checklists and, in some embodiments, at least some of the surgical pause checklists stored on the storage device are associated with one member of the medical team. In some embodiments, the touchscreen device can be configured to identify the associated surgical pause checklists for selection when the identity of the one member is determined by the processor. In some embodiments, the additional information stored on the storage device can include one or more foreign object counting systems and/or medical information relating to the patient.

In another embodiment, a method of identifying persons in an operating room is provided. The method includes receiving electronic sign-in information at a reader from a plurality of persons entering the operating room and processing the electronic sign-in information to identify respective names of the persons. The names of the plurality of persons can be displayed on an electronic display device. The method can further include receiving electronic sign-out information at the reader from one or more of the plurality of persons, the sign-out information indicating that the one or more of the plurality of persons is leaving the operating room, and removing from the electronic display device the names of the one or more persons for which electronic sign-out information has been received.

In some embodiments, the electronic sign-in information includes information about roles assigned to the plurality of persons for a surgical procedure and the method further includes displaying respective roles of the plurality of persons on the electronic display device alongside the display of names. In other embodiments, a time associated with the receipt of the electronic sign-in information is logged. In yet other embodiments, information can be entered on a touchscreen device relating to one or more additional persons to establish the presence of the one or more additional persons in the room, and the name of the one or more additional persons on the display device can be displayed.

In other embodiments, the method can include retrieving one or more surgical pause checklists from a database, selecting one of the one or more surgical pause checklists, and displaying the selected surgical pause checklist on the display device. In some embodiments, the method can further comprise displaying on the display device a count of foreign objects that have been used during a surgical procedure and entering information about the foreign objects on a touchscreen device to alter the count of foreign objects displayed on the display device.

The foregoing and other objects, features, and advantages of the invention will become more apparent from the following detailed description, which proceeds with reference to the accompanying figures.

BRIEF DESCRIPTION OF THE DRAWINGS

FIG. 2 is a view of an exemplary display of information that can be provided on a display device of an interactive display system.

FIG. 3 is a view of an exemplary display of information that can be provided on a display device of an interactive display system.

FIG. 4 is a view of an exemplary display of information that can be provided on a display device of an interactive display system.

FIG. 5 is a view of an exemplary display of information that can be provided on a display device of an interactive display system.

FIG. 7 is a view of an exemplary display of information that can be provided on a display device of an interactive display system.

DETAILED DESCRIPTION

Figure 1:
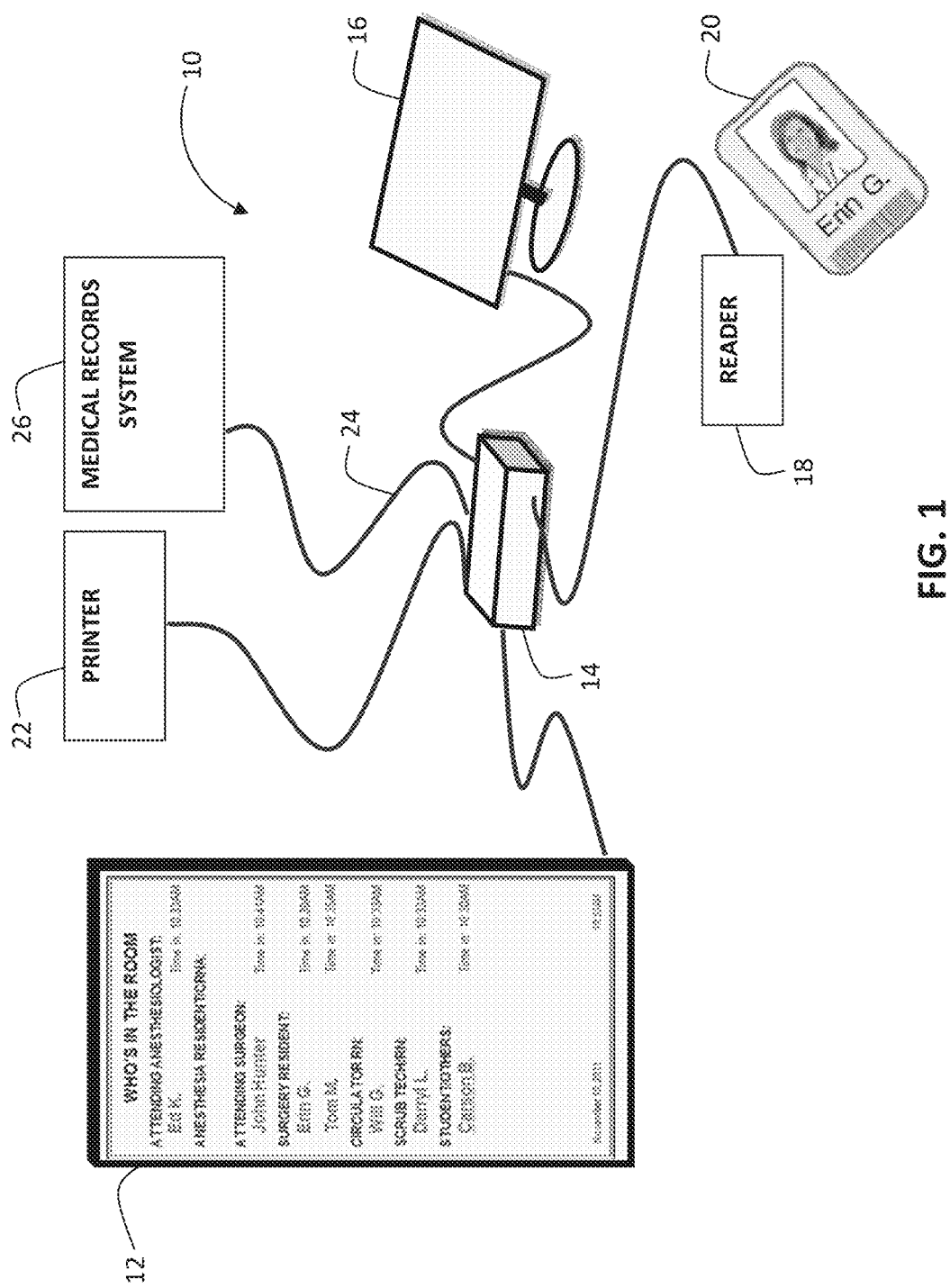
FIG. 1 is a schematic view of an embodiment of an interactive display system configured for use in an operating room.

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the terms "coupled" and "associated" generally mean electrically (wired or wirelessly), electromagnetically, and/or physically (e.g., mechanically or chemically) coupled or linked and does not exclude the presence of intermediate elements between the coupled or associated items absent specific contrary language.

As used herein, the terms "interactive display system" and "interactive methods of displaying" refer to systems and methods, respectively, that involve the display of information on an electronic display device in a manner that allows the displayed information to be updated based on direct or indirect interactions of one or more users with an input device, such as a touchscreen device or reader.

As used herein, the term "badge" refers to any physical item associated with, worn, or carried by a person which contains information about the identity of the person, including for example, access badges, smart cards, or other contact-type or contactless devices that contain identification information.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Moreover, for the sake of simplicity, the attached figures may not show the various ways (readily discernible, based on this disclosure, by one of ordinary skill in the art) in which the disclosed system, method, and apparatus can be used in combination with other systems, methods, and apparatuses. Additionally, the description sometimes uses terms such as "produce" and "provide" to describe the disclosed method. These terms are high-level abstractions of the actual operations that can be performed. The actual operations that correspond to these terms can vary depending on the particular implementation and are, based on this disclosure, readily discernible by one of ordinary skill in the art.

The systems and methods described herein provide significant improvements in the communication of information to and from medical personnel before, during, and after medical procedures. As described in more detail below, such improvements in communication can increase operational efficiencies and, at the same time, greatly improve patient safety.

As discussed above, operating rooms usually have a conventional "whiteboard" on which hospital personnel handwrite the names of persons who are, or will be, in the room for a given surgical procedure. Inaccuracies in the displayed information can occur when the information is incorrectly transcribed or when something changes (e.g., a change in the attending surgeon or other medical personnel) and the information on the whiteboard is not properly updated.

FIG. 1 is a schematic illustration of an embodiment of an interactive display system 10 configured for use in an operating room. System 10 can comprise a display device 12 that is connected (wired or wirelessly) to a computer system 14. The display device can comprise an electronic visual display that is sufficiently large for observation by multiple viewers. In some embodiments, display device 12 comprises a display screen that is 30 inches or larger as measured by diagonal length. In other embodiments, display device comprises a display screen that is 40 inches or larger as measured by diagonal length. Display device 12 can comprise a display screen that is generally impervious to dust, fluids, and pathogens so that the device can be disinfected between uses without risk of harm to the device and/or emitting pathogens or other harmful particles between cleanings.

Computer system 14 is not intended to suggest any limitation as to scope of use or functionality, as the methods described herein can be implemented in diverse general-purpose or special-purpose computing environments. Computer system 14 can include at least one processing unit for executing computer-executable instructions. Computer system 14 can also include memory (volatile memory, non-volatile memory, or some combination of the two) that can store software for implementing one or more of the methods described herein. In some embodiments, computer system 14 can serve as a data processing system for receiving information from an input (e.g., a reader or touchscreen device) and processing that information for delivery of related information to display device 12.

Computer system 14 can include one or more input devices. The input device(s) can include a touch input device that is configured to provide input to the computer system 14. As shown in FIG. 1, the touch input device can comprise a touchscreen device 16 that facilitates input of characters and other information to the computer system 14. Touchscreen device 16 can comprise any electronic visual display that can detect the presence and location of a touch within the display area for inputting information or otherwise making on-screen selections. Alternatively, or in addition to touchscreen device 16, other input devices can be provided, such as a keyboard, mouse, pen, or trackball, a voice input device, or other similar devices that provides input to the computing environment 100.

Computer system 14 can also include a reader 18 capable of receiving information from a user's badge 20 or other similar identification and/or information containing device. Reader 18 can comprise any device capable of reading information contained on the badge 20 or other such device. Reader 18 can have one or more sensing capabilities for receiving and/or detecting information associated with badges 20. For example, reader 18 can comprise a magnetic stripe reader, a proximity reader (e.g., contactless RFID reader), a barcode reader, a smart card (contact or contactless) reader, a near field communication (NFC) reader, or other similar information sensing systems. As noted above, reader 18 can deliver data received from a badge 20 to computer system 14 for processing of that data for delivery to display device 12. As described in more detail below, the data retrieved from the badge can contain identifying information about a user and/or a unique identifier that is associated with information stored apart from the badge through a badge registration process. Alternatively, reader 18 can comprise an internal, integrated computer system for processing and delivering such information to display device 12.

Computer system 14 can comprise one or more storage devices that can be removable or non-removable, including, for example, magnetic disks, magnetic tapes or cassettes, CD-ROMs, DVDs, USB flash drives, or any other medium which can be used to store information and which can be accessed by computer system 14. Such storage devices can store instructions for software configured to implement any of the described systems and methods.

In addition to display 12, computer system 14 can comprise additional output devices, such as a printer 22 that can provide output from computer system 14 to view selected media content. Computer system 14 can also comprise one or more communication connections 24 that enable media or data communication over a communication medium to another computing entity, such as a medical records system 26. Communication connection 24 can be configured to convey information such as software (computer-executable instructions), medical data or patient information, or other relevant data or information via modulated data signals. A modulated data signal is any signal that has one or more of its characteristics set or changed in such a manner as to encode information in the signal. By way of example, and not limitation, information conveyed via modulated data signals can include wired or wireless techniques implemented with an electrical, optical, RF, infrared, acoustic, or other carrier.

As discussed in more detail herein, interactive display system 10 can improve safety in operating rooms and other similar environments by increasing communication among members of a surgical team, thereby reducing a number of preventable problems. In particular, interactive display system 10 can improve the process of identifying staff members that are in the room during any medical procedure through the use of reader 18 and a visually accessible display 12. As a member of a surgical team enters or leaves an operating room, their badge 20 can be read by reader 18, processed by computer system 14, and information relating to that member can be displayed on display device 12. For example, if reader 18 is a proximity card reader, badge 20 can be moved close to the reader so that the reader can read badge 20 and identify the badge owner. Similarly, for example, if reader 18 is a magnetic card reader, a magnetic stripe on badge 20 can be swiped across the reader to identify the badge owner.

Once the information contained on badge 20 (or some portion thereof) is read by reader 18, information from badge 20 can be delivered to computer system 14 and displayed on display device 12. FIG. 2 illustrates an enlarged view of the display device shown in FIG. 1. As shown in FIG. 2, the members of the surgical team that have entered the room and "signed in" using the reader can be shown on display device 12. For example, FIG. 2 shows an exemplary display device that identifies the attending anesthesiologist ("Ed K."), attending surgeon ("John Hunter"), surgery residents ("Erin G.", "Tom M."), circulator RN ("Will G."), scrub techn/RN ("Darryl L."), and student/others ("Carson B.").

The information on each badge 20 of a user can include information about the user's role at the hospital and/or for the particular surgical procedure that is to be performed. For example, a badge 20 assigned to Dr. John Hunter can contain information that identifies him as a surgeon so that when that his badge 20 is read by reader 18, computer system 14 automatically assigns Dr. John Hunter the role of "attending surgeon" and displays his name on display device 12 accordingly. Alternatively, in some embodiments, the role of a person for a particular surgical procedure can be assigned based on a previously-identified role for that person for the particular surgical procedure that is to be performed. In that case, computer system 14 can recognize the previously-identified role assigned and, instead of associating the person with a general role identified by badge 20, computer system 14 can associate the person with the previously-identified role for the surgical procedure and display the person's name on display device 12 accordingly.

The information on badge 20 can contain the information as described above and/or it can be configured to have an identifier that can be used to associate badge 20 with user information stored elsewhere, such as on computer system 14. Thus, for example, badge 20 may contain a number (or other identifier) and that number can be linked or otherwise associated (e.g., registered) on computer system 14 with a particular user. Accordingly, after a badge is registered with a user (e.g., by manually associating a badge number with a name and/or pre-assigned role), upon scanning of a badge, the identifier is obtained by computer system 14 and information associated with that identifier (e.g., name, role, etc., of the user) is retrieved. Thus, the act of processing information or data read from the badge can comprise retrieving, from a source external to the badge, user identification information associated with a unique identifier stored on the badge.

In some embodiments, the categories of personnel in the room (e.g., attending anesthesiologist, attending surgeon, etc.) shown in the display can be pre-selected based on the surgical procedure that is to be performed. Thus, for example, if the surgical procedure does not require an attending anesthesiologist, the information provided on display device 12 can be configured so that there is no attending anesthesiologist category reflected on the display. In this manner, display device 12 can visually depict all required categories of personnel on the screen so that everyone in the room can see whether all required personnel are in the room or whether one or more personnel are not yet present. For example, if the display device 12 shown in FIG. 2 is part of a system that identifies only pre-selected categories of personnel, by viewing display device 12 it would be apparent that the required anesthesia resident/CRNA is not yet present.

Alternatively, instead of a pre-selected listing of categories of personnel, the categories shown on display device 12 can be reflective of the personnel that have already signed in and are present in the room. Thus, for example, as the attending surgeon arrives and registers his or her badge with reader 18, display device will add a category of "attending surgeon" to display device 12 (assuming no other attending surgeon has already signed in) and display the name of the attending surgeon in association with that category.

Figure 6:
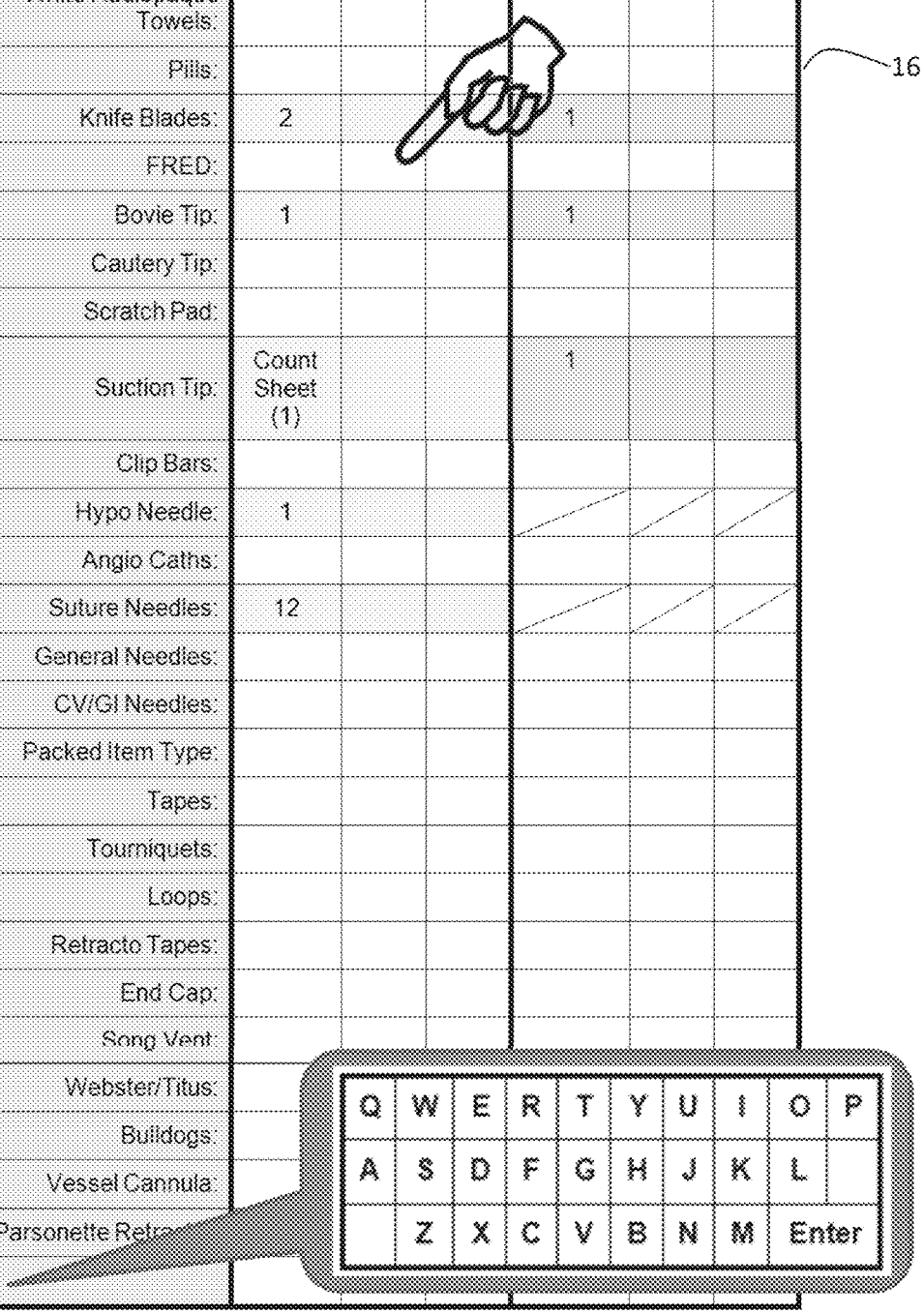
FIG. 6 is a view of an exemplary display of information that can be provided on a display device of an interactive display system.

In some embodiments, a touchscreen device 16 can be provided to facilitate the entry of information into system 10 instead of, or in addition to, reader 18. For example, FIG. 3 illustrates an embodiment where touchscreen device 16 is configured to receive input relating to the medical personnel attending the surgical procedure. When no reader is provided, information relating to the attending medical personnel can be directly input into system 10 by touchscreen device 16. For example, touchscreen device 16 can have a graphical user interface that comprises one or more drop-down lists. In this manner, categories of medical personnel can be provided and under each category a drop-down list of possible medical personnel is provided for selection. As each member of the surgical team enters the room, the circulating nurse (or other assigned personnel) can select the name of that person using touchscreen device 16, and computer system 14 will cause display device 12 to display the selected names (e.g., FIG. 2). If medical personnel leave the room, the circulating nurse (or other assigned personnel) can use touchscreen device 16 to remove the name of the departing person, thereby updating display device 12 to reflect that person's absence from the room. In the event that a person entering the room is not reflected in the drop-down lists, touchscreen device 16 can be provided with a text box and a keyboard (external or on-screen as shown in FIG. 6) through which the circulating nurse (or other assigned personnel) can enter that person's name, role, or other relevant information relating to that individual.

In some embodiments, touchscreen device 16 can be used in combination with reader 18. For example, as each person enters the room, they can scan their badge 20 with reader 18 and information relating to that person can be displayed on touchscreen device 16 and/or display device 12. Touchscreen device 16 can be used to confirm and/or alter information received from badge 20. Thus, for example, if reader 18 incorrectly identifies the role of a person entering the room (either through an error in the badge setup or because the person has been assigned a different role than usual for this procedure), the circulating nurse (or other assigned personnel) can change the information reflected on display device 12 using touchscreen device 16 in the manner noted above.

The identification of the arrival and departure of medical personnel can be logged and stored by computer system 14. In some instances it may be desirable to log some but not all of the arrival and departure activity of medical team members. For example, if it is known that one or more staff members may be entering and leaving repeatedly during the procedure for various reasons, it may not be desirable to continually log such information. In that instance, procedurally, it may be desirable to ignore some departure and arrival events and/or otherwise separately identify that person beforehand using an identifier such as "on-call," "potentially not in permanent attendance," or the like. If desired, the log of such activity can be printed (e.g., using printer 22) and/or can be transferred to another storage location (e.g., a USB drive).

In addition to providing improved accuracy relating to information about who is in an operating room at any time, interactive display system 10 can also improve the safety and efficiency of a surgical procedure by conveying other information relating to the surgical procedure.

FIG. 4 illustrates an embodiment in which a surgical pause checklist is received by computer system 14 and displayed on display device 12. Surgical pause checklists are commonly used to provide a standardized approach to identify goals and opportunities for medical safety enhancements in an operating room. In conventional procedures, such checklists are printed on paper that is attached to a wall in an operating room. During the procedure, the circulating nurse verbally confirms whether each item on the checklist has been completed. As shown in FIG. 4, interactive display system 10 can be configured to display a surgical pause checklist on display device 12. Because display device 12 is desirably in a location visually accessible by the team members, medical personnel in the room are provided with greater visual access to the surgical pause checklist, thereby improving review of the surgical pause checklist by each team member.

Selections relating to the surgical pause checklist can be made on any input device, such as touchscreen device 16. When a surgical pause checklist is selected from a menu on touchscreen device 16, the surgical pause checklist appears on the screen of the touchscreen device 16 and, desirably, is displayed on display device 12 so that other medical personnel in the room can visually view the surgical pause checklist. To facilitate review of the checklist, the system can be configured so that when an item from the surgical pause checklist is touched (or otherwise accessed by the input device) that item will appear zoomed in on the large screen display along with previously-checked items. Some checklist items can be provided with only a check box to check off the identified task, while others can have text boxes or the like to allow for the entry of other inputs (e.g., as shown in FIG. 6), such as the patient's name, the surgical procedure, etc.

In some embodiments, when the final item on the surgical pause checklist is checked off (or otherwise answered such as by marking the item as "NA" for non-applicable), the entire checklist can appear on the large screen display as shown in FIG. 4. In this manner, medical personnel can confirm that all necessary boxes have been checked and/or all other answers provided. The system can also automatically record the time that each item on the checklist was answered. Records relating to surgical pause checklists can be stored by computer system 14, printed (e.g., using printer 22), and/or can be transferred to another storage location (e.g., a USB drive).

FIG. 5 illustrates another view of display device 12, wherein at least a portion of the patient's consent form is displayed on display device 12. As shown in FIG. 6, the patient's consent form can be displayed along with general information relating to the surgical procedure that is to be performed. In some embodiments, such information displayed alongside the consent form can comprise a portion of the surgical pause checklist. Accordingly, by displaying the surgical pause checklist and consent form on the visually accessible display device 12, can improve communication within the operating room and help to reduce misunderstandings about the patient, the patient's concerns, and/or the procedure that is to be performed on the patient.

In some embodiments, interactive display system 10 can store and/or retrieve a plurality of surgical pause checklists. Thus, surgical pause checklists associated with numerous types of surgical procedures and/or with particular surgeons can be stored and conveniently retrieved for use. Upon selecting the attending surgeon, for example, a list of surgical pause checklists associated with that attending surgeon can populate on the screen of touchscreen device 16 (or another input device) as available for selection. In this manner, attending surgeons can prepare and select one or more surgical pause checklists and those checklists can be uploaded to the interactive display system 10 (or to a location accessible by the system such as medical records database 26) for ready access by medical personnel within the operating room.

The interactive display systems described herein can also be effective to improve safety and efficiency in avoiding the occurrence of retained foreign objects. In conventional surgical procedures, surgical tools are usually tracked by keeping count of tools that are brought into the surgical space and handwriting this tally on a whiteboard. After the surgery is completed, used instruments are reconciled against the whiteboard tally to determine whether or not any tools are missing. FIGS. 6 and 7 illustrate an embodiment in which surgical tools used during the procedure are more accurately and efficiently tracked using interactive display system 10.

FIG. 6 illustrates a screenshot of an input device (e.g., touchscreen 16) for entering information about tools (e.g., foreign objects) that have been opened for use and/or used during the surgery. As shown in FIG. 6, touchscreen 16 can have a "Foreign Objects" graphical user interface that allows an operator, such as the circulating nurse, to maintain a count of tools associated with the surgical procedure. In some embodiments, the Foreign Objects graphical user interface is configured to allow the operator to distinguish between objects associated with open packages (e.g., the category "Open Packages") and objects actually used during the surgery (e.g., the category "In Patient"). After loading the Foreign Objects graphical user interface, a preloaded table of potential surgical instruments can be loaded on the touchscreen 16. The operator can select (e.g., by touching) cells in the table to increment the number of associated tools in that cell. As noted above, separate columns can be provided to differentiate between open packages of tools and tools in use in the patient. In addition, color coding can be provided to indicate that a named tool row has been activated (e.g., one or more tools have been opened and/or used for the procedure).

As in other embodiments, text entry capabilities (e.g., an onscreen keyboard as shown in FIG. 6) can be provided to allow for identification of tools not reflected in the preloaded table of potential surgical instruments. In some embodiments, the preloaded tables can be selected from a plurality of available preloaded tables that are associated with the surgeon and/or the surgical procedure that is to be performed. In this manner, the preloaded list can more accurately reflect the types of objects that will be used during the surgical procedure.

As the operator enters tools using touchscreen 16, creating a tally of opened packages and/or used tools, those objects can be displayed on display device 12 so that other medical personnel in the room are readily aware of the objects in the room that could be potential retained within the patient. As with the entry screen on touchscreen 16, open packages and used tools can be identified in separate columns. In contrast to the graphical user interface of the touchscreen 16, however, the tables displayed on display screen 12 preferably do not include categories of objects that have not been selected. For example, as shown in FIG. 6, "white radiopaque towels" have not been selected. Therefore, the information displayed on display device 12 would not include a listing for "white radiopaque towels" since none have been opened or used.

A printable or saved log of foreign objects can be maintained listing the name and time objects were entered and/or subtracted from the tables. As with other information logged by interactive display system 10, this information can be stored by computer system 14, printed (e.g., using printer 22), and/or can be transferred to another storage location (e.g., a USB drive).

In some embodiments, interactive display system 10 can be linked to medical records system 26 via a communication medium so that additional information relating to the patient or medical procedure can be retrieved by computer system 14 and displayed on display device 12 in the operating room. For example, if the attending surgeon would like to review some portion of the patient's medical history on display device 12, the circulating nurse can make a selection on touchscreen device 16 and retrieve that patient's records from medical records system 26. Once retrieved by computer system 14, the circulating nurse can use touchscreen device 16 (or another input device) to select a medical record, or portion of a record, to be displayed on display device 12.

As discussed above, the various embodiments disclosed herein can greatly improve safety procedures within an operating room, or other similar environment, by facilitating communication of information regarding the patient, the surgical procedure, and/or the medical personnel involved in the surgical procedure. It should be understood that the various embodiments disclosed herein can be performed separately or, alternatively, combined so that one or more of the embodiments can be performed together. For example, in one embodiment, the interactive display system can be configured to function only to identify medical personnel who are in the room or otherwise involved in the surgical procedure (e.g., by using a reader and display device as shown in FIG. 1). In other embodiments, the interactive display system can be configured to provide this function and also provide the function of (1) selecting, displaying, and performing a surgical pause checklist, (2) selecting, displaying, and performing a retained object evaluation, and/or (3) selecting, retrieving, and displaying additional patient and/or surgical procedure information from a database (e.g., medical records system 26).

When display device 12 is configured to display the various aspects of the different embodiments described herein, an input device (e.g., touchscreen device 16) can allow an operator (e.g., the circulating nurse) to select which particular aspect should be displayed on display device 12. Thus, for example, the operator could select a surgical pause check for display on display device 12 (e.g., FIG. 4) and, after that checklist has been completed, switch to displaying the retained objects embodiment on display device 12 (e.g., FIG. 7). In addition, display device 12 can be configured to display multiple windows at a time to permit simultaneous display of two or more aspects described herein. Thus, for example, if it is desirable to display information about who is in the operating room (e.g., FIG. 2) throughout the procedure, that information can be display alongside other information, such as the surgical pause checklist, the retained object evaluation, and/or additional patient or surgical procedure information.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An interactive method of displaying information in an operating room in connection with a scheduled surgical procedure, the method comprising:
   receiving information about a plurality of categories of personnel that have been pre-selected as required for the scheduled surgical procedure;
   displaying each of the categories that have been pre-selected as required for the scheduled surgical procedure on a display screen;
   receiving data via a reader from one or more badges associated with one or more respective persons to establish the presence of the one or more persons in the operating room, the data containing identifying information relating to the one or more persons;
   processing the data received via the reader from the one or more badges of persons in the operating room; and
   displaying the identifying information from the data on the one or more badges on display device along with the pre-selected plurality of categories of personnel required for the surgical procedure, the identifying information including at least a name of the one or more persons established as being present in the operating room and a role assigned to the one or more persons for the surgical procedure;
   associating the identifying information and preselected categories together on the display screen to indicate whether all preselected categories of personnel are represented by one or more respective persons that have established their presence in the operating room;
   identifying the departure from the operating room of the one or more persons that had been previously established as present in the operating room;
   removing the departed one or more persons from the display of the identifying information such that the display screen accurately reflects all of the persons that are in the operating room;
   displaying on the display device a first count of foreign objects that have been opened and are available for use during the surgical procedure;
   displaying on the display device a second count of the foreign objects from the first count that have actually been used during the surgical procedure; and
   entering information about the foreign objects on a touchscreen device to determine the first and second counts displayed on the display device, the touchscreen device including a pre-determined listing of foreign objects from which the first and second counts can be selected,
   wherein the display device is visually accessible within the operating room, the display device comprising a display screen that is sufficiently large for observation by multiple viewers within the operating room.

2. The method of claim 1, further comprising:
   logging a time associated with the receipt of data by the reader from the one or more badges; and
   displaying the logged time along with the respective name and role of the one or more persons displayed on the display device.

3. The method of claim 1, further comprising:
   entering information on a touchscreen device relating to one or more additional persons to establish the presence of the one or more additional persons in the room, and
   displaying the name and the role of the one or more additional persons on the display device.

4. The method of claim 1, further comprising:
   retrieving one or more surgical pause checklists;
   selecting one of the one or more surgical pause checklists; and
   displaying the selected surgical pause checklist on the display device.

5. The method of claim 4, wherein the act of retrieving the one or more surgical pause checklists comprises identifying surgical pause checklists associated with at least one of the one or more persons in the operating room and retrieving the identified surgical pause checklists.

6. The method of claim 4, further comprising:
   displaying the surgical pause checklist on a touchscreen device;
   receiving inputs on the touchscreen device relating to a completion of one or more events on the surgical pause checklist; and
   altering the displayed surgical pause checklist displayed on the display screen to reflect the inputs received on the touchscreen device.

7. The method of claim 1, further comprising:
   retrieving patient data from a medical records system;
   selecting at least a portion of the patient data using a touchscreen device; and
   displaying the selected portion of the patient data on the display device.

8. The method of claim 1, further comprising:
   additionally displaying on the display screen at least one of (1) a surgical pause checklist and (2) a foreign object count while displaying the identifying information on the display device.

9. An interactive display system for use in an operating room in connection with a surgical procedure on a patient, the system comprising:
- a sign-in device that comprises a reader configured to capture data contained on a badge carried by members of a medical team using one or more data-sensing capabilities associated with the reader, the data-sensing capabilities being configured to identify members of the medical team that have entered the operating room;
- a processor configured to process the data read by the reader to determine respective identities of the members and respective roles of the members for a surgical procedure;
- a display device configured to receive and display preselected categories of required roles for the surgical procedure, along with the identities and roles of the members identified to have entered the operating room to ensure that all preselected categories of required roles are represented, the display device comprising a display screen that is 30 inches or larger as measured by a diagonal length such that the display screen is sufficiently large for observation by multiple viewers;
- a touchscreen device coupled to the processor; and
- a storage device for storing additional information thereon, wherein the touchscreen device is configured to receive inputs from a user to select one or more of the additional information stored on the storage device for display on the display device,
- wherein the additional information stored on the storage device comprises one or more foreign object counting systems device that include a pre-determined listing of foreign objects from which a listing of foreign objects can be selected and displayed.

10. The system of claim 9, wherein the additional information stored on the storage device comprises a plurality of surgical pause checklists.

11. The system of claim 10, wherein at least some of the surgical pause checklists stored on the storage device are associated with one member of the medical team, and wherein the touchscreen device is configured to identify the associated surgical pause checklists for selection when the identity of the one member is determined by the processor.

12. The system of claim 9, wherein the additional information stored on the storage device comprises medical information relating to the patient.

13. A method of identifying persons in an operating room for a scheduled surgical procedure, the method comprising:
- receiving information about a plurality of categories of personnel that have been pre-selected as required for the scheduled surgical procedure and displaying the categories on a display screen;
- receiving electronic sign-in information at a reader from a plurality of persons entering the operating room;
- processing the electronic sign-in information to identify respective names of the persons;
- displaying the names of the plurality of persons on an electronic display device in the operating room that is at least 30 inches in size when measured along a diagonal of the display device;
- receiving electronic sign-out information at the reader from one or more of the plurality of persons, the sign-out information indicating that the one or more of the plurality of persons is leaving the operating room;
- removing from the electronic display in the operating room device the names of the one or more persons for which electronic sign-out information has been received;
- logging one or more times associated with the receipt of the electronic sign-in information and the receipt of electronic sign-out information;
- displaying on the display device a count of foreign objects that have been used during a surgical procedure; and
- entering information about the foreign objects on a touchscreen device to alter the count of foreign objects displayed on the display device,
- wherein the electronic sign-in information includes information about roles assigned to the plurality of persons for a surgical procedure and compares them to a pre-selected list of roles required for the surgical procedure, the method further comprising displaying the pre-selected roles of the plurality of persons on the electronic display device alongside the display of names.

14. The method of claim 13, further comprising:
- entering information on a touchscreen device relating to one or more additional persons to establish the presence of the one or more additional persons in the room, and
- displaying the name of the one or more additional persons on the display device.

15. The method of claim 13, further comprising:
- retrieving one or more surgical pause checklists from a database;
- selecting one of the one or more surgical pause checklists; and
- displaying the selected surgical pause checklist on the display device.

* * * * *